(12) United States Patent
Glimelius et al.

(10) Patent No.: US 12,023,517 B2
(45) Date of Patent: Jul. 2, 2024

(54) METHOD OF ION PBS TREATMENT OPTIMIZATION, COMPUTER PROGRAM PRODUCT AND COMPUTER SYSTEM FOR PERFORMING THE METHOD

(71) Applicant: RaySearch Laboratories AB (Publ), Stockholm (SE)

(72) Inventors: Lars Glimelius, Stockholm (SE); Erik Engwall, Hagersten (SE); Otte Marthin, Uppsala (SE)

(73) Assignee: Raysearch Laboratories AB (publ), Stockholm (SE)

( * ) Notice: Subject to any disclaimer, the term of this patent is extended or adjusted under 35 U.S.C. 154(b) by 0 days.

(21) Appl. No.: 18/552,670

(22) PCT Filed: Feb. 17, 2022

(86) PCT No.: PCT/EP2022/053996
§ 371 (c)(1),
(2) Date: Sep. 27, 2023

(87) PCT Pub. No.: WO2022/207183
PCT Pub. Date: Oct. 6, 2022

(65) Prior Publication Data
US 2024/0082602 A1    Mar. 14, 2024

(30) Foreign Application Priority Data
Mar. 31, 2021    (EP) .................................. 21166245

(51) Int. Cl.
*A61N 5/10*    (2006.01)
(52) U.S. Cl.
CPC ......... *A61N 5/1031* (2013.01); *A61N 5/1043* (2013.01); *A61N 2005/1087* (2013.01)

(58) Field of Classification Search
CPC ................ A61N 5/1031; A61N 5/1043; A61N 2005/1087
See application file for complete search history.

(56) References Cited

U.S. PATENT DOCUMENTS

| 7,268,358 B2 | 9/2007 | Ma et al. |
| 9,220,920 B2 | 12/2015 | Schulte et al. |

(Continued)

FOREIGN PATENT DOCUMENTS

| CN | 101014383 A | 8/2007 |
| CN | 111936204 A | 11/2020 |
| WO | 2019164835 A1 | 8/2019 |

OTHER PUBLICATIONS

Martin Soukup et al., "A pencil beam algorithm for intensity modulated proton therapy derived from Monte Carlo simulations; A pencil beam algorithm for intensity modulated proton therapy", Phys in Med and Bio, vol. 50, No. 21, Nov. 7, 2005, pp. 5089-5104 (Year: 2005).*

(Continued)

*Primary Examiner* — Thaddeus B Cox
*Assistant Examiner* — Joshua D Lannu
(74) *Attorney, Agent, or Firm* — Noréns Patentbyrå AB (57) ABSTRACT

A computer-based method of providing a set of selected spots for use in ion radiotherapy optimization is proposed, the method comprising the steps of defining a number of positions in the volume, each position corresponding to a possible Bragg peak location, the positions being defined to provide coverage of the volume, for each position, for at least one beam direction, performing a ray trace to determine characteristics of a potential spot in the beam that will place its Bragg peak in the position and for each position, selecting zero, one or more of the potential spots, based on the characteristics, and including the one or more selected spots in the set of selected spots. The set of selected spots may be (Continued)

used in treatment planning. The invention also relates to computer program products and a computer system for performing the methods.

13 Claims, 3 Drawing Sheets

(56) References Cited

U.S. PATENT DOCUMENTS

| | | |
|---|---|---|
| 9,555,265 B2 * | 1/2017 | Schulte ............... A61N 5/1077 |
| 2021/0038914 A1 | 2/2021 | Traneus et al. |
| 2021/0101027 A1 | 4/2021 | Carabe-Fernandez et al. |

OTHER PUBLICATIONS

Martin Soukup et al., "A pencil beam algorith for intensity modulated proton therapy derived from Monte Carlo simulations; A pencil beam algorithm for intensity modulated proton therapy", Physics in Medicine and Biology, Institute of Physics Publishing, Bristol GB, vol. 50, No. 21, Nov. 7, 2005, pp. 5089-5104 XP020084413.
International Search Report and Written Opinon dated May 3, 2022, Europen Patent Office, Rijswijk, Netherlands.
Office Action dated Jan. 18, 2024 in corresponding Chinese application No. 202280011116.8, Beijing, China.

* cited by examiner

METHOD OF ION PBS TREATMENT OPTIMIZATION, COMPUTER PROGRAM PRODUCT AND COMPUTER SYSTEM FOR PERFORMING THE METHOD

TECHNICAL FIELD

The present invention relates to a computer-based method of preparing for treatment plan optimization for ion-based radiation treatments. The invention also relates to a computer program product for such optimization and a computer arranged to perform such optimization.

BACKGROUND

Ion based radiation treatments involve irradiating a patient with protons or heavier ions. This is often done in the form of Pencil Beam Scanning (PBS) treatments, which involve delivering radiation to the patient in the form of one or more beams from different beam directions. Each beam includes a number of spots delivered in essentially the same direction as the beam, where each spot is defined by its position, direction, weight and energy. The spot weight indicates the number of particles included in the spot and the energy determines how far the particles will travel in the patient. The direction and energy therefore determine where the Bragg peak of this spot will be located within the patient, that is, where most of its energy will be deposited.

One beam may comprise a large number of spots, up to several thousand, or even millions, and up to 50 energy layers. The direction of each spot may be adjusted by the use of magnets, so that the beam will cover a larger area of the patient. Each beam has a direction, which depends on the gantry position and angle as well as the position and orientation of the couch and of the patient lying on the couch.

An important part of ion-based radiation therapy planning is providing an initial set of candidate spots that may be used in the treatment plan. Both the spots and the energy layers should be close enough to each other to ensure uniform coverage of the target. At the same time, there are also disadvantages associated with using a large number of spots. Traditionally, spots are selected before optimization and set up so that each beam will cover the target with Bragg peaks. Especially for treatments involving multiple beams, such as ion arc treatment, this will result in a large number of spots having their Bragg peaks at the same position. This will lead to long initial dose computation times in the optimization as well as long optimization times.

SUMMARY OF THE INVENTION

It is an object of the present invention to provide a set of selected spots that will provide both good target coverage and acceptable computation and optimization times, thus facilitating treatment plan optimization.

The invention relates to a computer-based method of providing a set of selected spots for use in optimization of an ion beam radiation treatment plan suitable for providing radiation therapy to a volume of a patient, said radiation treatment plan involving one or more beam directions, the method comprising the steps of
  a. defining a number of positions in the volume, each position corresponding to a possible Bragg peak location, the positions being defined to provide coverage of the volume,
  b. for each position, for at least one beam direction, performing a ray trace to determine characteristics of a potential spot in the beam that will place its Bragg peak in the position, to determine a set of potential spots,
  c. for each position, selecting zero, one or more of the potential spots, and including the one or more selected spots in the set of selected spots.

This method of selecting spots to be used in a radiation treatment plan ensures that the spots will cover the target in the best possible way while reducing the number of spots by eliminating or combining spots that are located near another spot, and selecting the best possible beam direction for creating the spot. In this way, the redundancy of having multiple spots with their Bragg peaks in the same or almost the same position may be reduced.

In preferred embodiments, the positions are defined as Bragg peak locations, and each ray trace is performed to compute the radiological depth along the ray trace and is followed by the steps of determining the energy and position of the corresponding spot. The step of selecting one or more spots in this case involves distributing the spots over one or more of the beam directions so that each spot will have its Bragg peak in the desired position.

The positions may be defined by discretizing the volume into sub-volumes within the volume, wherein the ray tracing is performed to determine the projection of each sub-volume and the step of selecting one or more spots involves distributing the projected sub-volumes over one or more of the beam directions and selecting the spots from the projected sub-volumes per beam direction. Each sub-volume may be exactly one dose-grid voxel, or a number of dose-grid voxels. Each sub-volume may also be smaller than a voxel, for example a fraction of a voxel.

The selection in step c above may be performed in consideration of a least one of the following:
  distribution of spots over the one or more beam directions,
  distribution of spots within an energy layer,
  target intersection length,
  homogeneity index or heterogeneity index along the ray trace,
  energy sequencing,
  number of selected spots in the beam,
  in scenario-based robust optimization, the contribution of a spot created for one scenario in a different scenario, which will influence the robustness of the plan,
  distribution of other relevant quantities, such as high linear energy transfer values, and/or relative biological effectiveness inside the target volume.

The selection in step c may be based on a goodness measure defined for each of the potential spots, based on the characteristics of the respective spot. The goodness measure may be determined in any suitable way, for example based on the list above, and/or at least one of the following:
  the number of selected spots corresponding to a specific Bragg peak location,
  the number of selected spots in one beam,
  the position of the selected spot relative to a boundary of the target. This may be a distal or lateral boundary but it may also be a proximal boundary of the target.

The method may include defining at least one beam sector, each beam sector encompassing a set of adjacent beam directions forming a subset of the beams. This is particularly relevant for arc therapy but may also be applied to discrete, non-rotating beams, and will enable more exact control of the selection of spots, for example, by specifying the number of spots in each beam sector to ensure an even distribution, or deciding to avoid a particular beam sector that will interfere too much with a risk organ in the patient. The selection in step c above may then be performed with respect to the number of potential spots for the set of adjacent beam direction.

The method may comprise, for a first beam direction in the set of beams, or in one of the subsets of the beams, identifying the first energy and creating an energy layer for the first beam direction for the identified energy, creating subsequent energy layers with energies varying according to a predefined pattern and distributing the spots corresponding to a specific Bragg peak to the layers in dependence of their energies. In this way the plan may involve a sequence of energy layers that will reduce the total delivery time to the patient. In general, each energy layer change takes some time, so reducing the number of energy layer changes reduces the delivery time. Also, an increase in the energy takes longer than a decrease, so that it will be advantageous to the extent possible to start at a high energy layer and gradually reduce the energy.

The method may also, or alternatively, comprise a step restricting the number of energy layers in the set of beams or in each sector. This may be achieved by determining a maximum number of energy layers in the plan, and/or by setting a predefined separation between the energy layers. Limiting the number of energy layers will reduce the computation time of the plan and also the delivery time to the patient.

The invention also relates to a computer-based method for optimizing an ion beam radiation treatment plan, comprising providing a set of selected spots for use in the optimization by performing the method according to any one of the embodiments discussed in this document. The use of the set of spots selected as outlined above enables faster computation of a suitable and robust plan and also a plan that can be delivered to the patient in shorter time.

The invention also relates to a computer program product comprising computer-readable code means, preferably on a non-transitory storage medium, which, when run in a processor of a computer will cause the computer to perform the method according to any one embodiment of the invention, and to a computer comprising a processor and a program memory, wherein the program memory holds such a computer program product arranged to be run in the processor.

The spot selection algorithm may be used for setting up spots prior to optimization for ion beam treatments. It may be used for any type of ion beam treatment planning although it is especially useful for situations in which a large number of beams are used, such as ion arc treatments.

BRIEF DESCRIPTION OF DRAWINGS

The invention will be described in more detail in the following, by way of examples and with reference to the appended drawings.

DETAILED DESCRIPTION OF EMBODIMENTS

Figure 1:
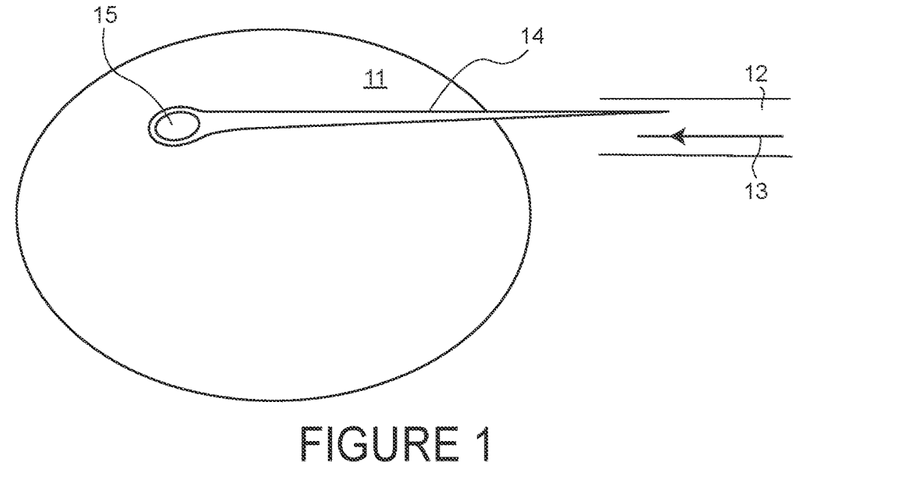
FIG. 1 illustrates schematically the relationship between a beam, a spot and a Bragg peak, with regard to a target in a patient being treated.
Figure 2A:
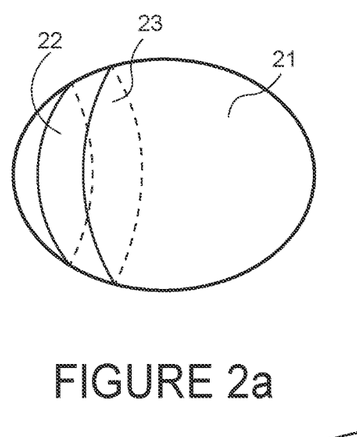
FIG. 2 shows a simplified example of the placement of Bragg peaks in a target.
Figure 2B:
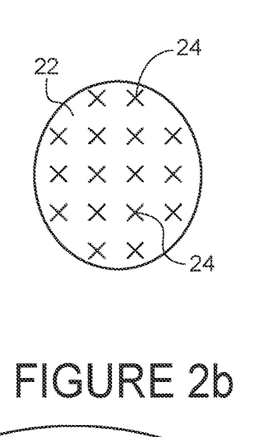
Figure 2C:
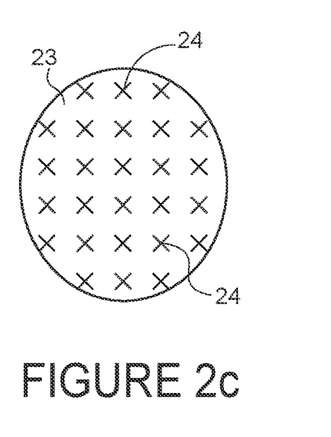
Figure 3:
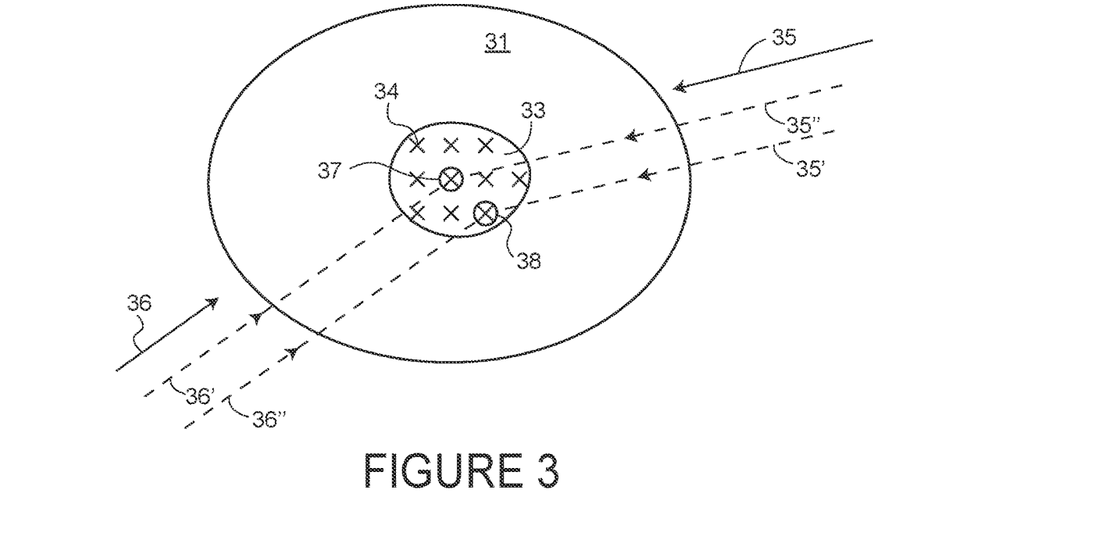
FIG. 3 shows how spots from two beams can contribute to the same Bragg peak in a target.

To explain the relevance of spot placement in treatment planning, FIGS. 1-3 illustrate various aspects of ion beam radiation treatment and treatment planning. In the discussion below, protons will be used as an example of ions.

FIG. 1 shows, schematically, a section through a target 11 to be treated with ion radiation therapy. In FIG. 1, one proton beam 12 from one beam direction shown by arrow 13 is shown. The beam comprises a number of smaller, narrow beam components called pencil beams 14. For the purpose of illustration, only one beam 12 and one pencil beam 14 are shown in FIG. 1. Instead of protons, another type of ions may be used, as is known in the art.

A spot is the 2D representation of a pencil beam on the isocenter plane. Each spot is defined by distributions around nominal parameters including a weight as well as by distributions around a nominal energy, a nominal position, and a nominal direction, which is roughly the same as the beam direction 13. The weight determines how many ions are in the spot. As is well known, an ion will deposit most of its energy near the end of its path, in a small volume known as the Bragg peak 15. The spot position, direction and energy determine where the spot will end, and thereby the position of the Bragg peak, which makes it possible to control with a certain accuracy where most of the spot's energy will be deposited. As will be understood, the position of the Bragg peak 15 can be reached from any beam angle, with the right energy. Therefore, it is possible for two or more spots from different angles to contribute to the dose in the same position in the target. As is well known, the geometry of the patient and the densities of tissues traversed will also affect the position of the Bragg peak, so this must be taken into account when distributing spots to cover the target.

FIG. 2 illustrates the concept of energy layers in a simplified case where all Bragg peaks having the same energy are shown as located at the same depth, which will only be the case if the traversed volume is homogeneous. In a realistic situation, the geometric depth of a Bragg peak will depend on the density of the tissues traversed so that Bragg peaks from spots in the same energy layer will be located at different geometric depths. a) shows a target 21 divided into energy layers. For illustration purposes, only two such layers 22, 23 are shown but the whole target should be covered by energy layers at a suitable distance from each other, to allow for Bragg peaks over the whole target volume. In b) and c), the spot positions 24 at the isocenter plane are shown given for the energy layers 22 and 23, respectively. For the purposes of this invention, instead of intended Bragg peak positions 24, the target volume may be divided into small subvolumes, the subvolumes being represented, for example, by one or more dose grid voxels, or by a fraction of a dose grid voxel.

FIG. 3 shows a cross-section of a patient 31 with a target 33 inside the patient's body. The target 33 is filled with intended Bragg peak positions 34. In this example, two beam angles 35 and 36 are shown, and two spots, 35', 35" and 36', 36" respectively, are shown for each beam angle. As can be seen, one spot from each angle, namely spots 35' and 36' will have their Bragg peaks placed in the same intended Bragg peak position 37 and will both contribute to the dose in this position. Likewise, one spot from each angle, namely spots 35" and 36" will have their Bragg peaks placed in a different intended Bragg peak position 38 and will both contribute to the dose in this position. The same will be true for each of the other intended Bragg peak positions 34. As will be understood, the same position can be reached from any beam direction, so if there are more beam directions there may be a large number of spots depositing energy in the same position 34, 37, 38. This is the case in particular for arc therapy, which may include beam directions covering a full 360° revolution. With directions 2° apart, as is a typical case, this means there will be 180 beam directions for a full revolution. With a continuous delivery during rotation, the arc might need to be discretized into even more directions in the spot selection step, for example, at 1° or 0.5° intervals. Instead of intended Bragg peak positions, the target volume may be divided into small subvolumes, for example the size of one or a few voxels.

The invention enables the selection of which beam direction or directions should have spots that will contribute to which intended Bragg peak positions, or subvolumes, respectively.

Figure 4:
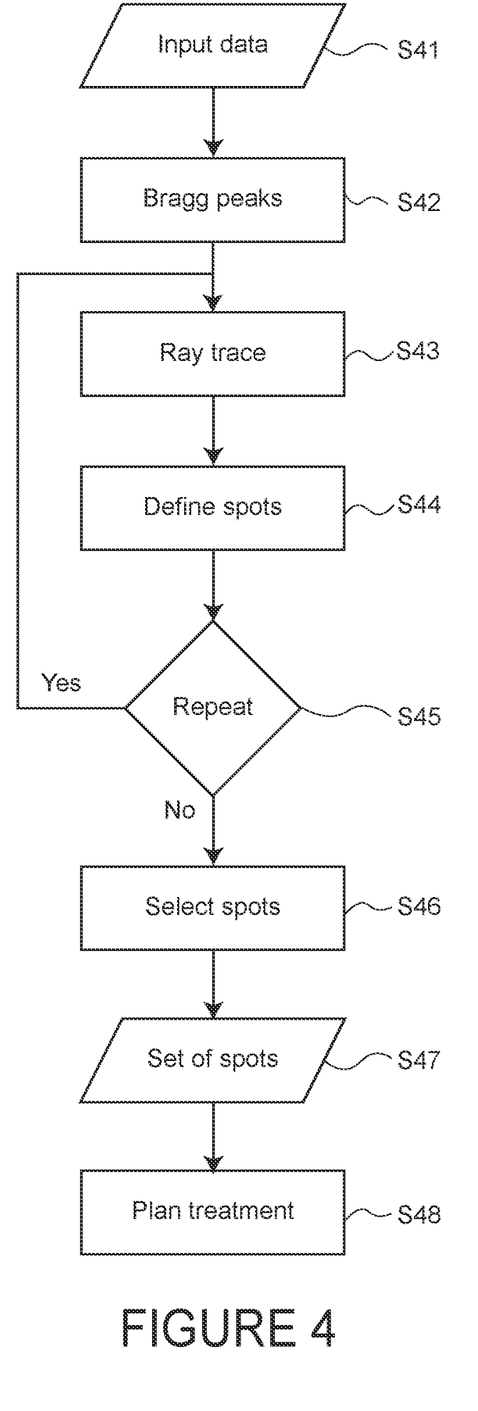
FIGS. 4 and 5 are flow charts of different embodiments of the method according to the invention.

FIG. 4 illustrates a first possible implementation of a method according to the present invention for determining a set of spots suitable for treatment planning and, optionally, using the set of spots in treatment planning. Input data S41 to the method includes information about a patient including a target volume and possibly tissue and organs surrounding the target volume. Input data for the subsequent raytracing also includes information about the type of treatment plan that is intended to be made based on the outcome of this method, including the number of beams and beam directions available and whether the treatment involves arc therapy treatment.

In a first method step S42, a number of Bragg peak positions are defined within the target volume. The aim is preferably that the target volume should be filled with Bragg peaks, meaning that the distance between the Bragg peaks should be small enough to ensure that a suitable and robust dose distribution can be achieved by varying the spot weights.

For each of the Bragg peak positions determined in step S42, the following sequence of steps S43-S45 is performed:

In step S43 a number of ray trace procedures are performed. For each Bragg peak position, one or more ray trace procedures are performed for each available beam direction, to determine the corresponding spot position and energy. The energy of the spot is computed from the radiological depth, which is dependent on the geometrical distance to the position as well as the densities of tissues traversed along this distance. On the basis of this, in S44, possible spots within the available beams are identified. In a decision step S45 it is determined if the procedure is to be repeated for another Bragg peak position. If yes, the procedure reverts to step S43 for another Bragg peak position, if no more Bragg peak positions should be included, the spots to be used in the plan are selected among the possible spots, in step S46.

The output S47 from step S46 is a set of selected spots selected among the possible spots. This set of candidate spots may be subsequently used in treatment planning as indicated by optional step S48.

For each selected spot, its initial weight may be set. In the simplest case, the same default weight, for example 1, may be used for all spots, but it will be possible to set different weights for the different spots to create initial weights that are close to the result of the optimization, which will reduce the number of iterations needed, thereby making the optimization process faster.

Figure 5:
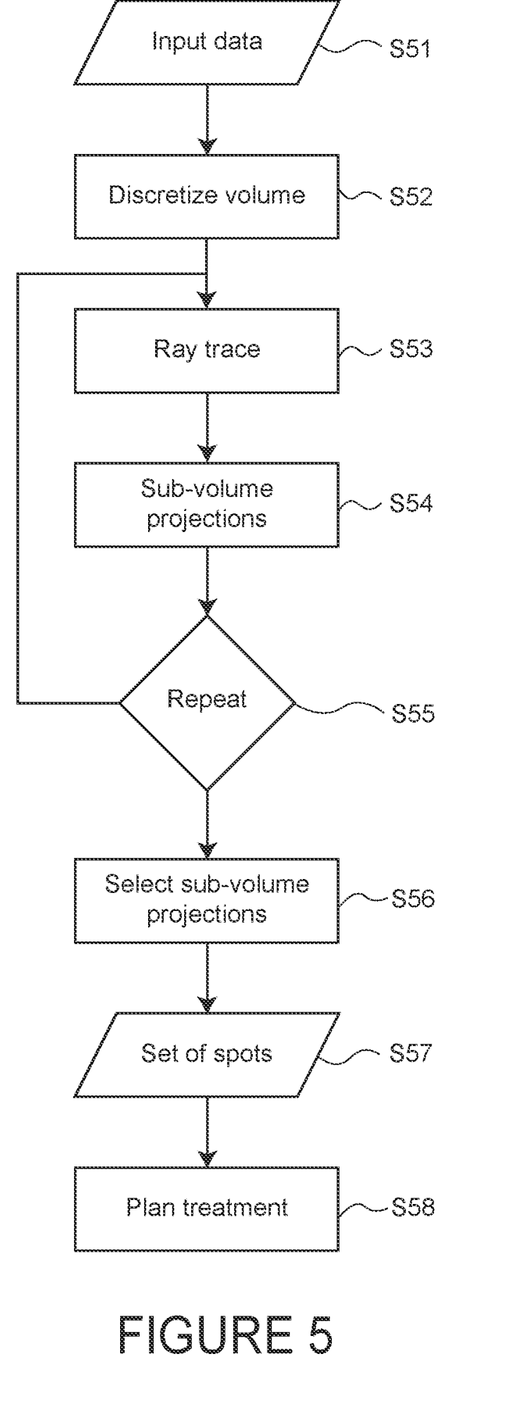

FIG. 5 illustrates a first possible implementation of a method according to the present invention for determining a set of spots suitable for treatment planning and, optionally, using the set of spots in treatment planning. Input data S51 is the same as in S41 above.

In a first method step S52, a number of subvolumes are defined within the target volume. Preferably, the subvolumes completely fill the target volume. Each subvolume may be a voxel or another suitable small volume and the size of the subvolume should be suitable for holding one Bragg peak, ensuring a suitable distribution of Bragg peaks within the target volume. Alternatively, a subvolume may be dimensioned to hold more than one Bragg peak, or there may be subvolumes without any Bragg peak, if the distance between Bragg peaks is greater than the size of the subvolumes.

For each of the subvolumes determined in step S52, the following sequence of steps S53-S55 is performed:

In step S53 a ray trace is performed for each available beam direction, to determine the projection of the subvolume for the beam direction in question, resulting in a possible subvolume projection for each beam direction the subvolume S54, each projection being defined by an energy and a position for the projection of the subvolume. A two-dimensional projection of a voxel in a particular beam direction is referred to as a bixel. In a decision step S55 it is determined if the procedure is to be repeated for another subvolume. If yes, the procedure reverts to step S53 for another subvolume, if no, in step S56, the subvolume projections to be used in the plan for each subvolume are selected among the possible subvolume projections for the subvolume in question and the set of spots is determined based on the subvolume projections.

The output S57 from step S56 is a set of selected spots. This set of selected spots may be subsequently used in treatment planning as indicated by optional step S58.

The selection of spots for one particular Bragg peak, or sub volume projections may be performed according to any suitable criterion, including one or more of the following:

the number of spots having a specific Bragg peak position. Limiting the number of spots having the same or almost the same Bragg peak position is a feasible way of limiting the number of spots while maintaining plan quality. In arc therapy, the number of spots per arc, or per sector, can be limited.

distribution of spots over the one or more beam directions. An even distribution may be desired. Alternatively, it may be desirable to increase robustness by selecting spots coming from a direction that will cause a minimum of change of the Bragg peak position if there are uncertainties in the patient setup, the patient anatomy. Spots that traverse a risk organ or an avoidance region may be excluded.

distribution of spots within an energy layer, based on a geometric measure with an objective to achieve better plan robustness or shorter delivery times.

target intersection length. It may be advantageous in many cases to select a spot that will pass through a long distance within the target, so that dose will be deposited in the target from the plateau, not only from the Bragg peak.

homogeneity index or heterogeneity index along the ray trace, since this will affect the robustness of the plan.

A homogeneity index or heterogeneity index is a measure of how the density varies along the spot central axis, as well as neighboring ray traces. Large variations in mass density along a trace, and large variations in density when comparing neighboring ray traces, will give a large heterogeneity index (or low homogeneity index). If the path of a spot is heterogeneous with respect to tissue density, a small change in position or orientation of the patient can affect the location of the Bragg peak of a spot from a particular direction and having a particular energy to a large extent.

sequencing of energy layers. The order of delivery of the energy layers could be planned to reduce the delivery time. The changing of energy layer of a beam takes time and therefore the number of such changes should be restricted if possible.

Also, in many types of equipment, the time required for changing to a lower energy layer is considerably lower than the time required for changing to a higher energy layer. Therefore, it is feasible in many cases to start at a high energy layer so that most changes will involve changing to a lower energy layer.

number of other spots that can be assigned to the same energy level and beam direction as the candidate spot. The shape of a target volume usually means that projections near its distal and proximal edges have small areas and therefore include few Bragg peaks and therefore few potential spots. If a beam involves only one, or a few, candidate spots, it may be feasible to select a spot in another beam direction instead, where other spots could fall into the same energy range. Since the assignment of a spot introduces restrictions on the energy, selecting a spot might lead to selecting an energy that restricts the possible choices of spots too much. It could lead to only having a single spot for the given beam direction, whilst if the spot would be assigned another beam direction, other spots could have fallen in the same energy range. In practice, it may be advantageous to include the spots for these Bragg peaks in a beam from a different direction in which these Bragg peaks are included in a larger group of Bragg peaks. Since the goal is to select each Bragg peak a number of times given a set of beam directions and energies per direction, one may want to select spots in a way that does not restrict the available beam directions and energies too much.

An even distribution of spots over the beam directions may be achieved by defining a number of beam sectors each beam sector comprising a set of adjacent beam directions, such that all beam directions within a certain angular interval, for example 30°, 60° or any other suitable range. This would make it possible to ensure that one candidate spot was located within each beam sector, thus distributing them across the whole set of beam directions. The division of beam directions into beam sectors may also be used to ensure that any change to the energy layers can be from a higher to a lower level as often as possible, by ensuring that the first energy layer applied for the first beam direction in each beam sector is the highest possible. In this way a limited number of changes to a higher level will be ensured.

In addition to the above, it may be feasible to select spots for which a small change in spot position will not result in a large change to the plan that is subsequently developed, as this will make the resulting plan more robust to unknown factors regarding position and/or tissue density affecting the water equivalent thickness traversed by a spot. For example, for a Bragg peak close to the edge of a target volume, a spot for which this Bragg peak is close to the distal edge of the target may be inappropriate. The Bragg peak of a spot travelling in a first direction through the volume towards its distal edge may end up outside of the volume, for example, if the position of the volume changes slightly, or in if the water equivalent thickness is slightly different, causing the spot to travel a bit farther than assumed. This may even lead to the Bragg peak being located in an organ at risk. Such a risk also occurs if there is a density gradient in tissue close to the Bragg peak, which means a position change may lead to a large geometrical change in the Bragg peak position. In such cases it will be feasible to select a spot from a beam direction at an angle, for example 90° compared to the first direction.

In addition to the Bragg peak position, which is based on the physical depth dose distribution, additional points and/or intervals may be computed along the ray trace, corresponding to threshold values of other distributions. These may include, for example, dose-weighted Linear Energy Transfer (LET D) above a certain value, and/or Relative Biological Effectiveness (RBE). It may also be computed from a combination of distributions, e.g. intervals where the physical dose and LET D are both above threshold values.

These additional points and intervals can be considered in the spot selection. For example, the selection of spots whose corresponding high LETD falls within an avoidance region may be avoided, or conversely, spots having their high LET D region inside an ROI, for example, the central part of a target, may be purposely selected.

In order to select the most suitable spots according to the criteria above, and/or other criteria, a goodness measure may be defined and determined for each potential spot. The goodness measure could be based on just one of the criteria or on a combination of two or more of the criteria.

Embodiments of the method according to the invention may also be combined with scenario-based robustness, in which different scenarios are defined regarding unknown factors such as the position and orientation of the patient, the tissue density, and both interfractional and intrafractional patient anatomy changes to ensure a set of candidate spots that will provide sufficient plan quality given different combinations of these factors.

In the case of arc delivery, an energy layer may actually be delivered during rotation of the gantry, which means that it can be delivered over an angular interval instead of over one angle. Typically, this angular interval will be 1°-2°. Therefore, robustness with respect to delivery angle may advantageously be taken into account.

Robustness may also be increased by computing, for each of the energy layers and each of their respective spot positions, what additional spot positions are required to achieve each spot position for all considered combinations of setup errors. creating a cloud of spots around each nominal spot position for each direction and each Bragg peak. It is also possible to use one or more ripple filters to spread each Bragg peak over a longer distance in the direction of the beam, which will reduce the number of spots needed to cover the target. Such use of ripple filters per se is known in the art.

Advantageously, the distribution of energy layers should be considered, as this affects the delivery time of the resulting treatment plan. For some common types of delivery machines, the change from one energy layer to another during the delivery of a plan takes time, which means that delivery of a plan involving many such changes will take a long time. In particular, a change to a higher energy layer may take several seconds, whereas a change to a lower energy layer may be done in a shorter time, typically about one second. To save time, it is also advantageous to plan the spots so that the energy layer may be changed at the same time as the beam angle.

In addition, the order of the energy layers may be selected to reduce delivery time. For example, the highest energy layer to be applied may be assigned to a spot in the first beam to be delivered, or the first beam in a selected sequence of beams, the energy decreasing for each subsequent beam. While it may not be feasible to plan the spots with a consistently decreasing energy for all beams, the spots may be selected to reduce the number of energy layer changes, and in particular to limit the number of changes to a higher energy layer. Although the example here assumes that a gradual reduction of the energy will be the most feasible, it will be understood that any suitable distribution of energy layers may be realized in this way.

Figure 6:
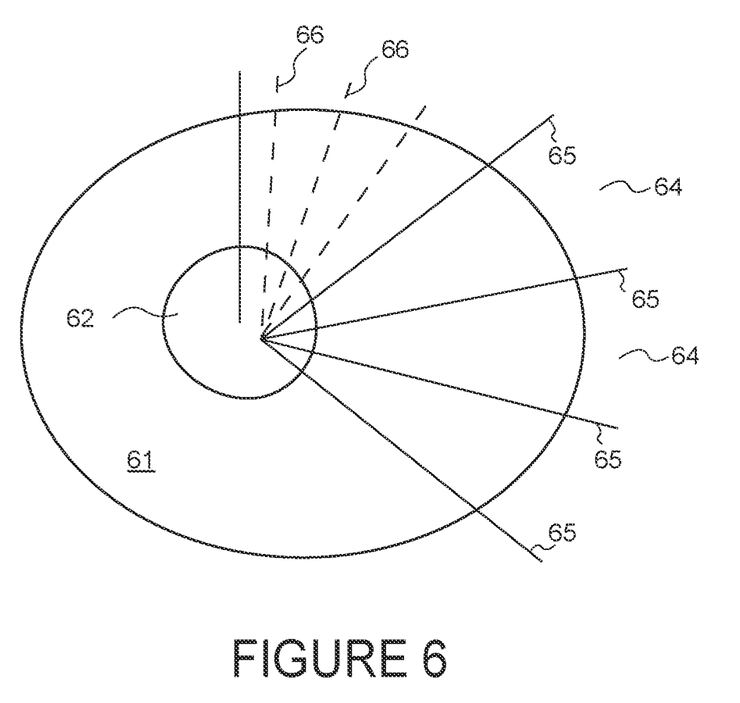
FIG. 6 illustrates the division of the beam directions into segments.

FIG. 6 is a simplified illustration of an embodiment. As in FIG. 3, a cross-section of a patient 61 is shown, including a target 62. In this example the set of beams has been divided into a number of beam sectors 64, shown limited by lines 65 in FIG. 6. Each beam sector 64 covers an angular interval including one or more adjacent beams 66. This may be done for different purposes, as will be discussed in the following. For example, the sectors may be used to ensure that a particular Bragg peak is covered by spots from different directions, by selecting spots to cover the Bragg peak in different sectors. One, or a specified number of spots in each sector may be selected, or a specified number of spots may be selected from a number of different sectors, which may or may not be adjacent. In many cases it will be advantageous to select spots in sectors or beams that are not adjacent, to ensure that the Bragg peak is covered from different directions. This will increase the robustness of the resulting plan.

The sectors may also be used to facilitate a suitable sequence of energy layers to ensure a suitable distribution of energy layers for the whole plan. As explained above, for many types of equipment the change from one energy layer during the delivery of a plan to another takes time, which means that delivery of a plan involving many such changes will take a long time. In particular a change to a higher energy layer may take several seconds, whereas a change to a lower energy layer may be done in a shorter time, typically about one second. To save time, it is also advantageous to plan the spots so that the energy layer may be changed at the same time as the beam angle. For example, the highest energy layer to be applied may be assigned to a spot in the first beam in a sector, the energy decreasing for each subsequent beam in the sector. When the next sector is reached, the first beam can again be used for the highest energy layer. Although the example here assumes that a gradual reduction of the energy will be the most feasible, it will be understood that any suitable distribution of energy layers within the sector may be realized in this way.

It is also possible to avoid using any beams in a particular sector, for example, because of the risk of these beams affecting an organ at risk in the patient.

The angular interval of each beam sector may be selected according to any suitable set of criteria. For example, the set of sectors that generates the largest average gap between the maximum and minimum energies over all sectors may be chosen. This may advantageously be applied to increase the chance of constantly reducing the energy during rotation, since energy reductions generally are faster than increases.

The set of sectors could also be based on how the depth of the most distal part of the target varies between beam directions. If the distance to the most distal edge increases too much with beam direction it may not be feasible to get both a monotonic change of energy between beam directions and include all Bragg peaks at the same time. This could be considered when setting up sectors, since it could make some beam directions unfeasible to exist in the same sector.

The set of sectors could also be selected taking into account how the water equivalent target thickness varies between beam directions. Such variations mean that an energy layer in a spot from a direction where the water equivalent target thickness is small may fill up a larger part of the target volume than an energy layer from a direction where the water equivalent target thickness is large. It may be advantageous to select a sector in such a way as to minimize the number of energy layers needed in a beam to cover the whole target from the beam direction To avoid or restrict dose delivered to an organ at risk, OAR, an OAR range margin may be applied to forbid the selection of spots that are unacceptable, for example, because they would result in a beam passing through or stopping in or within a range margin in front of risk organs. One way to achieve this could be, for each Bragg peak and beam direction, computing the water equivalent depth to the most proximal unacceptable position by the above definition for all images. This depth could then be compared with the depth of candidate spot itself. Another way would be to discretize the space of possible spot positions, and for each of these, and each beam direction and image compute the water equivalent depth to the most proximal unacceptable position by the above definition. Candidate spots could then be filtered by comparing their depth with the maximum acceptable value as computed above. In either case, this invalidation of spots must also be applied to the selected spots, since those include new spot positions introduced when considering setup errors as previously described.

For practical reasons, when creating energy layers, it should be ensured that the number of energy layers is kept at a reasonable level. To achieve this, a maximum number of energy layers may be set, in combination with the separation between maximum and minimum energies. Alternatively, the separation between allowable energy layers can be defined by a predefined energy step, expressed as WET, and each energy layer that is to be created can be adjusted to the nearest allowable energy layer.

The invention claimed is:

1. A computer-based method of providing a set of selected spots for use in optimization of an ion beam radiation treatment plan suitable for providing radiation therapy to a volume of a patient, the radiation treatment plan involving one or more beam directions, the method comprising:
   a. defining a number of positions in the volume, each position corresponding to a possible Bragg peak location, the positions being defined to provide coverage of the volume,
   b. for each position, for at least one beam direction among the one or more beam directions, performing a ray trace to determine characteristics of a potential spot in at least one beam that will place its Bragg peak in the position, to determine a set of potential spots, and
   c. for each position, selecting zero, one, or more of the potential spots, and including the selected potential spots in the set of selected spots.

2. The method of claim 1, wherein the positions are defined as Bragg peak locations, wherein each ray trace is performed to compute a radiological depth along the ray trace, and further comprising:
   determining an energy and a position of the potential spots along the ray trace,
   wherein selecting, zero, one, or more of the potential spots includes distributing the selected potential spots over one or more of the beam directions.

3. The method of claim 1, wherein the positions are defined by discretizing the volume into sub-volumes, within the volume, wherein the ray tracing is performed to determine a projection of each sub-volume and selecting one or more potential spots includes distributing the projected sub-volumes over one or more of the beam directions and selecting the spots from the projected sub-volumes per beam direction.

4. The method of claim 1, wherein the selection in step c is performed in consideration of a least one of the following:
- distribution of selected spots over the one or more beam directions,
- distribution of selected spots within an energy layer,
- target intersection length,
- homogeneity index or heterogeneity index along each ray trace,
- sequencing of energy layers,
- number of selected spots in the beam,
- in scenario-based robust optimization, a contribution of a spot created for one scenario in a different scenario, and
- distribution of high linear energy transfer values and/or relative biological effectiveness inside a target volume.

5. The method of claim 1, wherein the selection in step c is performed based on a goodness measure defined for each of the potential spots, based on characteristics of the respective potential spot.

6. The method of claim 5, wherein the goodness measure is determined based on at least one of the following:
- distribution of potential spots over the one or more beam directions,
- distribution of potential spots within an energy layer,
- target intersection length,
- homogeneity index or heterogeneity index along each ray trace,
- sequencing of energy layers,
- number of selected spots in the beam,
- in scenario-based robust optimization, a contribution of a spot created for one scenario in a different scenario,
- distribution of high linear energy transfer values and/or relative biological effectiveness inside a target volume,
- a number of selected spots corresponding to a specific Bragg peak location,
- a number of selected spots in one beam, and
- respective positions of the one or more selected spots relative to a boundary of the target.

7. The method of claim 1, comprising defining at least one beam sector, each beam sector encompassing a set of adjacent beam directions among the one or more beam directions, forming a subset of beams.

8. The method of claim 7, wherein the selection in step c is performed with respect to a number of potential spots for the set of adjacent beam directions.

9. The method of claim 1, comprising, for a first beam direction in a set of beams, or in a subset of beams, identifying a first energy and creating an energy layer for the first beam direction for the identified energy, creating subsequent energy layers with energies varying according to a predefined pattern and distributing the selected spots corresponding to a specific Bragg peak to the layers in dependence of their energies.

10. The method of claim 1 comprising a step restricting a number of energy layers in a set of beams or in a sector, by performing at least one of: determining a maximum number of energy layers in the plan, and setting a predefined separation between the energy layers.

11. A computer-based method for optimizing an ion beam radiation treatment plan, comprising providing a set of selected spots for use in the optimization by performing the method according to claim 1.

12. A computer program product comprising:
- a non-transitory computer readable storage medium containing computer-readable code means, which when run in a processor of a computer will cause the computer to perform the method according to claim 1.

13. A computer comprising a processor and a program memory, wherein the program memory includes instructions that when run by the processor cause the computer to perform the method according to claim 1.

* * * * *